United States Patent [19]

Subramanyam et al.

[11] Patent Number: 5,629,276
[45] Date of Patent: May 13, 1997

[54] COMPOSITION OF ALKYL PYRROLIDONE FOR SOLUBILIZING ANTIBACTERIALS

[75] Inventors: Ravi Subramanyam, North Brunswick; Ben Gu, East Brunswick, both of N.J.

[73] Assignee: Colgate-Palmolive Company, New York, N.Y.

[21] Appl. No.: 568,701

[22] Filed: Dec. 7, 1995

Related U.S. Application Data

[63] Continuation of Ser. No. 239,810, May 9, 1994, abandoned.
[51] Int. Cl.⁶ .................. C11D 3/20; C11D 3/26; C11D 3/48
[52] U.S. Cl. .................. 510/133; 510/131; 510/141; 510/155; 510/447; 510/450; 510/500; 422/37; 514/424
[58] Field of Search .................. 252/542, 106, 252/544, DIG. 5; 514/424; 422/37; 510/131, 133, 141, 155, 447, 450, 500

[56] References Cited

U.S. PATENT DOCUMENTS

| | | | |
|---|---|---|---|
| 4,455,250 | 6/1984 | Frazier | 252/106 |
| 4,576,729 | 3/1986 | Paszek et al. | 252/106 |
| 4,946,618 | 8/1990 | Knochel et al. | 252/117 |
| 4,975,218 | 12/1990 | Rosser | 252/117 |
| 5,008,038 | 4/1991 | Merianos et al. | 252/363.5 |
| 5,093,031 | 3/1992 | Login et al. | 252/357 |
| 5,154,849 | 10/1992 | Visscher et al. | 252/174.15 |
| 5,158,699 | 10/1992 | MacGilp et al. | 252/132 |
| 5,177,110 | 1/1993 | Oechslein et al. | 514/594 |
| 5,234,618 | 8/1993 | Kamegai et al. | 252/106 |
| 5,258,304 | 11/1993 | Carpenter et al. | 435/264 |
| 5,415,810 | 5/1995 | Lee et al. | 252/545 |

FOREIGN PATENT DOCUMENTS

| | | |
|---|---|---|
| 0433909 | 6/1991 | European Pat. Off. . |
| 2001768 | 10/1969 | France . |
| 1285449 | 8/1972 | United Kingdom . |
| 2243615 | 11/1991 | United Kingdom . |

OTHER PUBLICATIONS

Hitoshi Saski, et al., "Acute Toxicity and Skin Irritation of Pyrrolidone Derivatives as Transdermal Penetration Enhancer", Chen. Pharm. Bull., (1990) vol. 38, No. 8, 2308–2310.

Helioff et al, Alkyl Pyrrolidone Surfactants in Reactive Hair Care Products, Cosmetics & Toiletries, vol. 103, No. 5, p. 80, May 1988.

Hornby et al, Surface Active Specialty Solvents, Soap/Cosmetics/Chemical Specialities, Sep. 1992.

Helioff et al, Shampoo Innovation Via a New Surfactant, Drug Cosmetic Industry, Apr., 1988.

International Specialty Products, Brochure Entitled Surfadone LP Specialty Solvents and Surfactants, 1992.

International Specialty Products, Surfadone LP–300 Tentative Sales Specifications and Summary of Toxicity Information, 1992.

International Specialty Products, Surfadone LP–100 Tentative Sales Specifications and Summary of Toxicity Information, 1992.

*Primary Examiner*—Douglas J. McGinty
*Assistant Examiner*—Gregory R. Delcotto
*Attorney, Agent, or Firm*—Martin B. Barancik

[57] ABSTRACT

In accordance with the invention there is a composition comprising a. an antibacterial agent, and
b. a solubilizing effective amount for the purposes of solubilizing b of a compound or the formula.

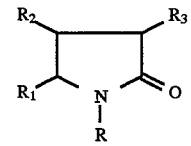

wherein R is alkyl of four to twenty carbon atoms inclusive and $R_1$, $R_2$, and $R_3$ are the same or different and are hydrogen or alkyl of one to twelve carbon atoms, inclusive.

15 Claims, No Drawings

COMPOSITION OF ALKYL PYRROLIDONE FOR SOLUBILIZING ANTIBACTERIALS

This is a continuation of application Ser. No. 08/239,810 filed May 9, 1994, abandoned.

BACKGROUND OF THE INVENTION

Personal cleansing compositions have been used for many years since the advent of lye. These compositions have been improved by utilizing various milder but still heavily foaming and cleansing surfactants as well as the addition of various additives such as fragrances, colors and fairly recently, antibacterial agents. These antibacterial agents serve to reduce the numbers of bacteria on the surface such as skin or even hard surfaces such as bathrooms and kitchens. Such bacteria includes staph aureus and s.epidermis. Many of these compositions are aqueous based whether they be in liquid form or solid such as bars. Most of the antibacterial agents are organic in nature and are therefore at least somewhat incompatible in the aqueous environment of a cleansing composition, be it for the skin or hard surfaces such as sinks and toilets. Examples of these antibacterial agents include the aromatic chloro carbanilides such as Trichlorocarban and various phenolic compounds such as Triclosan. Quite small amounts of these antibacterial agents are utilized in the cleansing compositions, usually less than 1.5 wt % of the composition. Therefore in order to obtain proper consistency of the entire composition, it is important to provide a proper solublizing material for these antibacterial agents. This is particularly important in a solid bar composition.

In the past it has been found that the use of Trichlorocarban in quantities to bring about a significant antibacterial action in cleansing compositions having a soap utilized polyethylene glycol such as PEG 12 as a solubilizer. However, these particular compositions involving the Trichlorocarban and the polyethylene glycol needed heating of the solubilizing mixture and the Trichlorocarban to a temperature in the mid-80° C. range to bring about the appearance of proper solubilization. Additionally if allowed to stand for a significant period of time, the solubilized Trichlorocarban could become somewhat unstable under high moisture conditions thereby forming chloranilines.

A new solublizing agent for antibacterial compounds has been discovered. This material allows for successful solubilization of the antibacterial agent at a substantially lower temperature than the mid 80° C. In fact such solubilization can occur at room temperature with Trichlorocarban. Additionally the material retains its stability while being exposed to significant levels of moisture. As measured by various antibacterial test systems, the cleansing composition with the antibacterial agent and particular solubilizing material is effective against staphaureus in both an in vitro test system as well as an in vivo forearm washing study.

SUMMARY OF THE INVENTION

In accordance with the invention there is a composition comprising a. an antibacterial agent, and b. a solubilizing effective amount for the purposes of solubilizing said antibacterial agent of a compound of the formula

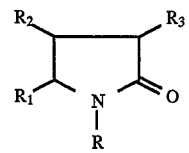

wherein R is alkyl of four to twenty carbon atoms inclusive and $R_1$, $R_2$, and $R_3$ are the same or different and are hydrogen or alkyl of one to twelve carbon atoms, inclusive.

A further aspect of the invention is the above-identified composition in admixture with a surfactant, wherein c is other than b. Examples of such surfactants are soap and other anionic surfactants. Such admixtures are useful in personal cleansing compositions, preferred, and hard surface cleansing compositions.

DETAILED DESCRIPTION OF THE INVENTION

With respect to the formula above, R is preferably alkyl of 6 to 14 carbon atoms inclusive and $R_1$, $R_2$, and $R_3$ are the same or different and are preferably hydrogen or alkyl of 1 to 8 carbon atoms, inclusive. Alkyl can be normal or branched, preferably normal. The most preferred compounds of the formula are those wherein IR is 8 to 14 carbon atoms and $R_1$, $R_2$, and $R_3$ are each hydrogen. Compounds of the formula are readily obtained from International Specialty Products and are known as Surfadone Lp-100 wherein R is 8 carbon atoms and $R_1$, $R_2$, and $R_3$ are hydrogen and Lp-300 wherein R is 12 carbon atoms and $R_1$, $R_2$, and $R_3$ are hydrogen. In each case the R group is normal alkyl. With respect to the overall composition wherein c is present, quantities of b can vary from about 0.05 to 20 wt. %, preferably about 0.8 to 8 wt % of the composition.

The amount of the antibacterial agent (a) and component (b) can vary according to the specific agent (a) and component (b) as long as the antibacterial agent is effectively solubilized. Generally any of (a) up to about 25 wt % or even higher of (a) can be solubilized in (b) component. Higher amounts of (a) can be solubilized in (b) if the solibilization system is heated up to a temperature wherein the components still maintain their stability. Solubilization of TCC in surfactant (b) of 35 wt. % or higher can be achieved at a temperature of 65°–70° C.

The surfactant group is extremely broad and any material which meets the usual definition of surfactant, i.e. reduces the surface tension of water, can be used. Examples of such surfactants include but are not limited to soaps such as long chain alkyl carboxylate salts, other anionics such as long chain sulfonates, long chain sulfates, zwitterionic materials such as betaines, sultaines, taurates, phosphates, nonionic surfactants such as alkanolamides, alkyl polyglycosides, and in general all those surfactants which are disclosed in U.S. Pat. No. 5,139,781 column 5, line 35 to column 11, line 46 all of which are incorporated by reference herein.

The (c) surfactant quantities are not critical to the invention. Quantities of surfactant of from about 1–99 wt %, preferably about 5–95 wt % of the composition can be employed.

As is noted from the structural formula, the solubilizing agent for the antibacterial compound is a pyrrolidone. Such material is prepared by standard techniques known in the art.

Any organic antibacterial compound which can be compatible with a cleansing composition utilized on skin or on the hard surface areas of the bathroom and kitchen can be employed. Examples of such antibacterials agents include the halo carbanilides as shown below in the formula.

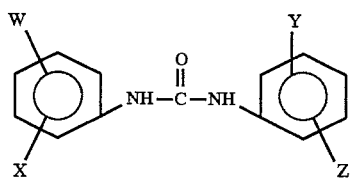

wherein W, X, Y and Z are the same or different and are halogen, trifluoromethyl or hydrogen. Halogen is fluoro, chloro, bromo, or iodo. The preferable halogen are chloro or bromo, most preferably chloro. Generally three of W, X, Y and Z are halogen and/or trifluromethyl, preferably all halogen. The most preferable compound of the formula is generically known as triclocarban or trichlorocarbanilide; CAS number 101-20-2. With respect to the schematic formula above, triclocarban occurs when W is meta chloro, X is para chloro, Y is para chloro and Z is hydrogen.

Additionally, phenolic compounds such as those of the formula can also be employed:

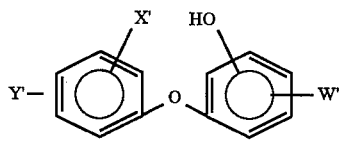

In this formula, W', X', and Y' can be the same or different and are halogen, trifluoromethyl or hydrogen. Halogen is fluoro, chloro, bromo or iodo. The preferable halogen are chloro or bromo most preferably chloro. Generally at least two of W', X' and Y' are halogen and/or trifluormethyl, preferably halogen. The most preferable compound of the formula is generally known as Triclosan, CAS number 3380-34-5. 2,4,4'-trichloro -2'-hydroxy diphenyl ether.

An antibacterially effective amount of the agent can be employed. Generally from about 0.01 to 5 wt %, preferably about 0.1 to 2 wt % of the three component composition can be employed.

As stated previously the use of pyrrolidone compounds of this invention allow an easy and complete, or essentially complete, solublization of the antibacterial agent followed by successful incorporation into a cleansing composition. The cleansing composition can ultimately be in the form of a solid or a liquid. If it is in the form of a solid, it is preferably in a bar form which can be readily held in the hand. If it is liquid, the composition can be within a container which is readily held in the hand and wherein the cleansing composition is delivered to the surface by an aerosol type compositon i.e. under pressure, a hand actuated delivery system such as a push mechanism or a hand squeeze mechanism and a shower gel container attached to a wall of a tub or shower. Use of the composition in shaving creams or gels is also contemplated. The composition may be delivered in any liquid form including a pasty or gel like material. For cleaning hard surfaces such compositions can be delivered to the surfaces by any method which is actuated by the hand including the aformentioned methods utilized for personal care compositions. The materials may be in the form of a liquid, gel, mousse, emulsion, lotion, or whatever desirable composition for delivering to the surface to be cleansed. The composition is usually aqueous based.

One of the advantages of utilizing the solubilizing material of the invention is that the solubilization can ocur at room temperature or slightly above, for example, up to about 50° to 70° C. In the context solubilization means disolving a solute. The solubilization should provide a composition which is clear, colorless, and stable, particularly with respect to moisture. A single phase generally occurs. There should be no solid material, i.e. precipitate, present in the mixture. This mixture can then be added to the additional surfactant composition together with any other materials which might be present in the composition such as, fragrances, colors, stabilizers, extenders, emolients, free fatty acids and other materials which ordinarily appear in a cleansing compositon.

Below is a table which compares the solubility of trichlorocarban (TCC) utilizing the compound of the invention compared to the generally employed compound PEG 12. PEG12 is a polyethylene glycol having 13 ethoxy groupings. LP100 is the pyrrolidone of the invention wherein R is normal alkyl of 8 carbon atoms and $R_1$, $R_2$, $R_3$ are each hydrogen. LP300 is the same compound except that R is normal alkyl of 12 carbon atoms.

TABLE I

| | Solubility of TCC | | | |
|---|---|---|---|---|
| Solvent | Solubility wt % | Mixing Temp °C. | Color | Stability |
| PEG 12 | 20 | 83 | Yellow | Precipitates upon standing 3–7 days |
| LP-100 | 30 | 45 | Colorless | stable |
| | 25 | RT | | |
| LP-300 | 26 | RT | Colorless | stable |

As shown by the data in Table I, the TCC is substantially more soluble in the pyrrolidone at a lower temperature and brings about a clear, colorless, stable composition.

The TCC pyrrolidone compositons are tested for antibacterial efficacy in an in vitro zone of inhibition test.

The test used to measure the antibacterial activity of the composition is a typical zone of inhibition test (Disc Diffusion Method) utilizing Staphylococcus aureus (ATCC 6538) conducted according to the following procedure.

I. Preparation of Test Organism

Organisms (S. aureus) are grown in 10 ml of Tryptic Soy Broth (substituted for Antibiotic Medium 3) for 24 hours at 37 C.

II. Preparation of Plates

The base layer is prepared with Tryptic Soy Agar (substituted for Antibiotic Medium 2). 20 ml of prepared agar is dispensed into 25 mm test tubes and sterilized. Pour the agar into heavy bottom Petri dishes and allow to solidify undisturbed.

Trypic Soy Agar is used to prepare the seed layer. 100 ml of prepared agar is dispensed into a screw capped flask. After sterilization the flask is cooled to 45° C. in a water bath.

2 ml of bacterial culture (in Part 1) is inoculated into Seed Agar. The seed agar is gently mixed and maintained at a temperature of 45° C. Pipet 7 ml of the seed agar onto the Base Agar plate and evenly cover the surface.

III. Preparation of Sample

Penicillin assay discs are inoculated with 20 microliter of sample (4% soap solution) by using a micropipet i.e. discs are air-dried in a disposable petri dish at RT for one hour.

IV. Placement of Disc and Reading of Zone

The discs with different samples are placed on seeded plate. Control discs are treated with 4% 60/40 (soap)/3.5/3.5 (free fatty acid) soap solution. Replicates of 3 plates are tested. The plates are incubated for 24 hours at 37° C. The diameter of the zones of inhibition is measured using Omega Slide Caliper in mm; Nl indicates no inhibition.

The higher reading of zone inhibition indicates the greater antibacterial activity. In the tables below the following abbreviations are used:

Soap—a long chain alkylcarboxylate salt mixture comprised of 60 wt % tallow based soaps and 40 wt % coco based soaps. Also present is 7 wt % free fatty acids. The remainder of the composition is water, PEG12—polyethylene glycol having average MW 600 TCC is Triclocarban; 3,4,4'trichlorocarbanilide.

TABLE II

Antibacterial Efficacy (In Vitro)
Zone of Inhibition Test Against S. aureus

| Formula | Zone (mm) |
|---|---|
| 60/40/7 soap (I.S.) | No inhibition |
| 1.5TCC/I.S. | 9.0 +/− 0.2 |
| 0.7TCC/2.8PEG 12/I.S. | 9.6 +/− 0.3 |
| 0.7TCC/2.8LP-100/I.S. | 9.8 +/− 0.1 |
| 0.7TCC/4.0LP-300/I.S. | 9.8 +/− 0.1 |
| 0.53TCC/2.8LP-300/I.S. | 9.2 +/− 0.1 |

From this data it is readily observed that solubilized TCC has higher antibacterial efficacy than TCC without solubilizer and solubilized TCC in PEG 12 is about equal to TCC in surfadone.

As is observed from the data the solubilized TCC has significant antibacterial efficacy in vitro.

A study utilizing the TCC pyrrolidone test system in an in vivo forearm washing study was performed against staph aureus. The panelists underwent a one-week washout period in which they refrained from using products containing active antibacterial ingredients in soaps, shampoos, deodorants, lotions etc. During the test phase, the panelists' forearms were washed with the placebo and 3 test soaps sequentially by a technician. Each of the panelists inner forearms were divided into 2 sections: the upper and the lower aspect of the volar forearm. Each site was washed for 60 seconds with either a test soap or the placebo based on a randomized schedule. After each wash, the sites were rinsed for 15 seconds and dried with paper towels. Each site was washed a total of 7 times over 3 days (3 washes each on Days 1 and 2 and 1 wash on Day 3). Each daily wash was separated by at least 1 hour.

Five minutes after the last wash, bacteria ($10^6$ organisms) were applied to a 4.52 $cm^2$ area of each washed site and occluded with a plastic chamber and secured to the skin with Tegaderm adhesive for 5 hours. After that time, bacteria were harvested by the method of Williamson and Kligman (J. Invest. Dermatol., 45, 498, 1965) and the skin degermed with 70% alcohol.

The effectiveness of the test soaps was determined by how well they inhibited bacterial growth compared to the placebo or to each other after incubation in 35° C. aerobic chamber.

An ANOVA was used to determine whether there was overall significant differences. Since significant differences were observed at p≦0.05, Fisher's PLSD was used to determine which products were different from each other. The results are shown in table III below.

It should be noted that the specific solubilization system utilized in the comparison examples below is a preferred combination of polysorbate, "poly" and PEG 12.

TABLE III

Against S. aureus

| Sample | Mean Log (n=16) CFU/cm2 +/− SEM | Log Reduction |
|---|---|---|
| Placebo | 4.15 +/− 0.31 | |
| 0.3% TCC Poly./PEG12 | 2.52 +/− 0.31 | 1.63 |
| 0.2% TCC Poly./PEG12 | 2.60 +/− 0.27 | 1.55 |
| 0.2% TCC LP-300 | 2.46 +/− 0.31 | 1.69 |

An additional study against s. epidermis was performed under the same procedure. The results are shown in Table IV below.

TABLE IV

| Sample | Mean Log (n=16) CFU/cm2 +/− SEM | Log Reduction |
|---|---|---|
| Placebo | 5.19 +/− 0.05 | |
| 0.3% TCC Poly./PEG12 | 3.13 +/− 0.32 | 2.06 |
| 0.2% TCC Poly./PEG12 | 2.99 +/− 0.19 | 2.20 |
| 0.2% TCC LP-300 | 2.68 +/− 0.16 | 2.51 |

As can be seen from each of these in vivo studies, the solublized TCC in component b has greater directional efficacy.

We claim:
1. A composition comprising
   a. an antibacterial agent selected from the group consisting of trichlorocarbanilide and 2,4,4,'-trichloro-2'-hydroxy diphenyl ether, and
   b. a solubilizing effective amount for the purposes of solubilizing said antibacterial agent of a compound of the formula

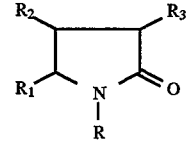

wherein R is alkyl of four to twenty carbon atoms inclusive and $R_1$, $R_2$, and $R_3$ are the same or different and are hydrogen or alkyl of one to twelve carbon atoms, inclusive.

2. The composition in accordance with claim 12 wherein a is trichlorocarbanilide.

3. The composition in accordance with claim 2 wherein a is soluble in b up to an extent of about 35 wt %.

4. The composition in accordance with claim 1 wherein there is an additional surfactant other than component b present in the composition.

5. The composition in accordance with claim 4 wherein a is trichlorocarbanilide.

6. The composition in accordance with claim 5 wherein the additional surfactant is about 5–95 wt % of the composition.

7. The composition in accordance with claim 1 wherein R is eight to fourteen carbon atoms, inclusive, and $R_1$, $R_2$ and $R_3$ are hydrogen.

8. The composition in accordance with claim 2 wherein R is eight to fourteen carbon atoms, inclusive, and $R_1$, $R_2$ and $R_3$ are hydrogen.

9. The composition in accordance with claim 3 wherein R is eight to fourteen carbon atoms, inclusive, and $R_1$, $R_2$ and $R_3$ are hydrogen.

10. The composition in accordance with claim 4 wherein R is eight to fourteen carbon atoms, inclusive, and $R_1$, $R_2$ and $R_3$ are hydrogen.

11. The composition in accordance with claim 5 wherein R is eight to fourteen carbon atoms, inclusive, and $R_1$, $R_2$ and $R_3$ are hydrogen.

12. The composition in accordance with claim 6 wherein R is eight to fourteen carbon atoms, inclusive, and $R_1$, $R_2$ and $R_3$ are hydrogen.

13. The composition in accordance with claim 10 wherein the antibacterial agent is present in quantities of from about 0.02 to about 5 wt. % of the composition.

14. The composition in accordance with claim 12 wherein the antibacterial agent is present in quantities of from about 0.01 to about 5 wt. % of the composition.

15. A method for cleansing skin which comprises applying to skin a composition of claim 14.

* * * * *

UNITED STATES PATENT AND TRADEMARK OFFICE
CERTIFICATE OF CORRECTION

PATENT NO. : 5,629,276
DATED : May 13, 1997
INVENTOR(S) : Ravi Subramanyam, et al It is certified that error appears in the above-identified patent and that said Letters Patent is hereby corrected as shown below:

Title page, item

[54] Should read "Composition of Antibacterial Agent with N-Alkylated Pyrrolidone"

Page 4, Column 6, line 32, Claim 1 Should read "A solid composition comprising..." (The word "solid" was originally omitted in the patent).

Signed and Sealed this

Twenty-ninth Day of May, 2001

Attest:

NICHOLAS P. GODICI

*Attesting Officer*  *Acting Director of the United States Patent and Trademark Office*